United States Patent [19]

Villalta et al.

[11] Patent Number: 5,081,983

[45] Date of Patent: Jan. 21, 1992

[54] MEDICAL RETRACTOR DEVICE

[76] Inventors: Josue J. Villalta, 11923 Discovery Cir., Indianapolis, Ind. 46236; Jean R. Passemard, 8 Rue Dela Tour Aux Saints, Crecy la Chapelle, 77580, France

[21] Appl. No.: 481,282

[22] Filed: Feb. 20, 1990

[51] Int. Cl.$^5$ .............................................. A61B 17/02
[52] U.S. Cl. ........................................ 128/20; 128/17; 606/198
[58] Field of Search ............................ 128/17, 18, 20; 606/197, 198

[56] References Cited

U.S. PATENT DOCUMENTS 3,750,652  8/1973  Sherwin .................. 128/20
4,667,657  5/1987  Kulik et al. ............. 128/20

FOREIGN PATENT DOCUMENTS 1700    1/1900  Fed. Rep. of Germany ........ 128/17
445162  2/1949  Italy ....................... 128/17
464302  6/1951  Italy ....................... 128/17

Primary Examiner—Edward M. Coven
Assistant Examiner—Mark S. Graham
Attorney, Agent, or Firm—Woodard, Emhardt, Naughton, Moriarty & McNett

[57] ABSTRACT

Retractor for wounds, incisions or cavities, with the retractor having a plurality of at least three detachable blades which open out one from another upon actuation of a single control, thereby forming a polygonal aperture. The opening mechanism is contained in a box situated outside the operating field. The present invention is more specifically intended for use in abdominal surgery or, in the gynecological field, for vaginal and cervical surgery or examination.

11 Claims, 4 Drawing Sheets

MEDICAL RETRACTOR DEVICE

BACKGROUND OF THE INVENTION

1. Field of the Invention

The invention relates to medical or veterinary equipment and, more precisely, to retractor apparatus for opening and maintaining open wounds or incisions or cavities in humans or in animals. The apparatus is primarily intended for use in the field of abdominal surgery and, in the gynecological field, as a speculum, for vaginal and cervical examinations or surgery.

2. Description of the Prior Art in the Abdominal Surgery Field

Apparatus called retractors are customarily used in surgical operations, during which, once the incision has been made, the tissues must be disengaged and held back in order to expose, for example, the abdominal cavity. The cavity thus exposed is kept open until the surgery has been terminated. The surgical retractors used up until now consist of a plurality of independent retractable blades, each blade usually having a long handle attached to a supporting ring, this ring being fixed to the operating table by means of an extension rod and a support-post. Various improvements have been made to these retractors, making it unnecessary for assistants or nurses to hold them, and also making it possible to provide different degrees of opening with the same equipment. The disadvantage inherent in the design of these retractors is that the device carrying the retractor blades and the parts which serve to support this device inevitably restrict access to the area requiring surgery. Inadequate exposure is a hindrance to the operator and can be particularly dangerous in microsurgery, where, the surgeon's visibility being limited by the optical instruments that he is using and, since he must manipulate without visual information in the zone where he moves his hands, it is of extreme importance that the area situated outside the opening should be completely unimpeded.

In the field of abdominal surgery, the present invention aims at providing a new type of apparatus, which meets practical requirements better than did past retractors and, in particular, by freeing access to the wound or incision opening, enables the surgeon to exert the required pressure, without assistance, at the said opening.

3. Description of the Prior Art in the Gynecological Field

Apparatus called speculums are customarily used in gynecology when a medical examination or surgery is needed. This is because the vagina walls are normally closed together, so that visual observation is practically impossible.

Vaginal speculums, as we know them, consist of a pair of blades, one of which can be adjusted in relation to the other in order to induce a widening of the vaginal cavity for examination, treatment, or possible surgery of the vagina or of the cervix.

Speculums present three disadvantages inherent in their design.

The First Disadvantage

During an examination or surgery using a speculum, a large part of the cavity is obscured by the blades themselves. This type of design obliges the surgeon to carry out several examinations or operations, displacing the speculum a little at each time in order to see or accede to all the surface of the vagina walls and of the cervix.

Having no reliable reference-points, the surgeon cannot be sure whether he has effected a thorough examination, with the possible end result of very serious errors in diagnosis.

The Second Disadvantage

The handle on which the blades are pivotally mounted and those parts serving to maintain the blades in an open position inevitably restrict access to the opening and lessen visibility of the area to be examined, treated, or on which the surgery is to be performed.

The Third Disadvantage

In order to increase the very limited force that the speculum itself applies to the opening, surgeons have recourse to other apparatuses such as weighted retractors or hand-held retractors. The former (weighted retractors) are very simplistic and may slide or slip out; as for the latter system, necessitating a third party, it is costly, unstable and an added encumbrance for the surgeon. In the gynecological field, the present invention aims to meet practical requirements more efficiently and more safely than past speculums have done up to now, particularly insofar as it exposes a maximum surface area of tissue, maximizes the visual field and, thirdly, allows the operator to exert sufficient pressure for the required degree of opening to the cavity, without any assistance.

SUMMARY OF THE INVENTION

The present invention consists of a plurality of narrow, finger-like blades, articulated and connected to the main mechanism in such a way that, when the said blades are simultaneously opened out after their introduction into the cavity, the skin and flesh surrounding the incision, wound or cavity are, as a result, disengaged and held back to the required degree of opening. During and after this manuever, the apparatus leaves the opening entirely clear. The advantages obtained through this invention are the following.

Firstly, the wound, incision or cavity can be gradually opened until the required degree of opening is reached.

Secondly, this can be done by one operator alone, using a single control.

Thirdly, the visual field inside the opening is maximized.

Fourthly, the area surrounding the opening is left clear.

The invention is shown hereafter in more detail in diagrammatic form. These diagrams, however, only represent three possible types of design. It should be understood that these diagrams and their related descriptions are only given as examples to illustrate the invention and do not in any way constitute a limitation.

FIG. 1 shows the front view of an assembled apparatus, conform with the present invention and based on the first type of design.

FIG. 7 shows the front view of an assembled apparatus, conform with the present invention and based on the second type of design.

DESCRIPTION OF THE PREFERRED EMBODIMENT

As indicated above, the present invention is in no way limited to the types of design and application described in more detail hereafter; it can be extended to any possible variations that the technician might envisage, within the framework and range of the present invention.

FIRST TYPE OF DESIGN

Figure 2:
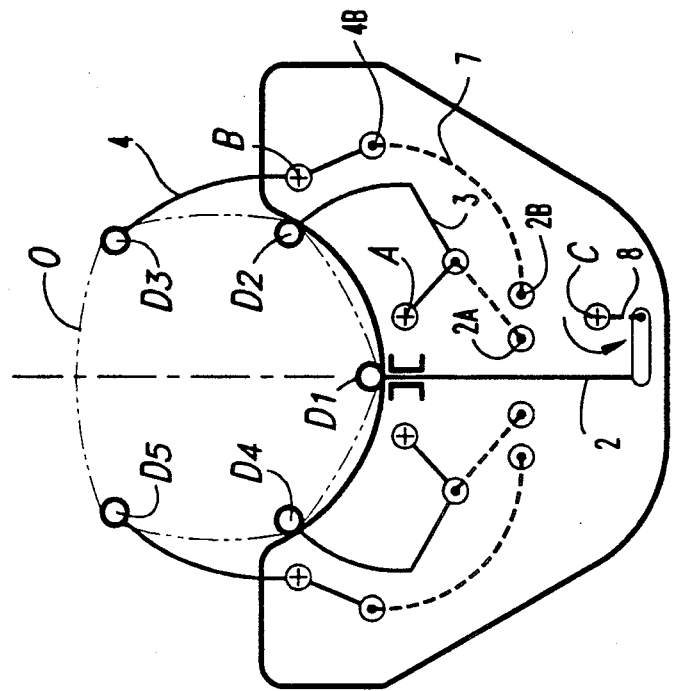
FIG. 2 is the same view as FIG. 1 only showing the retractor in the open position.
Figure 1:
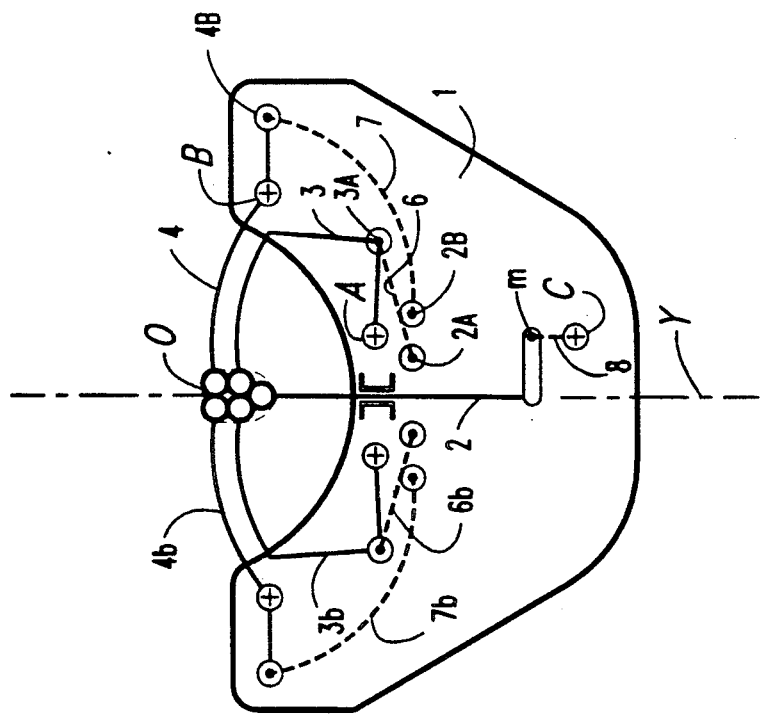
FIG. 1 is a diagrammatic front view of the preferred embodiment of the medical retractor in the closed position.
Figure 3:
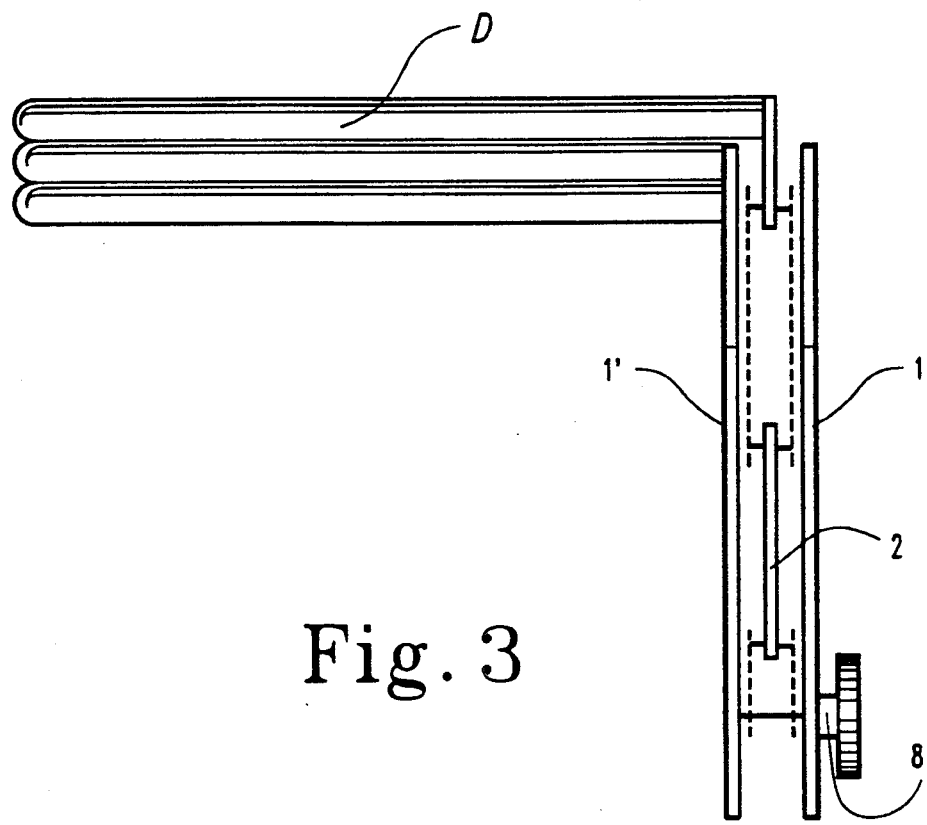
FIG. 3 is a side view of the retractor of FIG. 1 in the closed position.

The apparatus based on the first type of design is shown as follows:

FIG. 1: front view, closed position;
FIG. 2: front view, open position;
FIG. 3: side view, closed position.

The apparatus comprises four parts,
a supporting box
the mechanism proper
the blades
the opening and closing device, as follows:

A supporting box, comprising two flanges 1 and 1', which are about 12 cm. in height and 16 cm. in width. These flanges are about 2 mm. thick and they are kept apart by spacers.

The total thickness of the box thus formed is to the order of 1.6 cm.

The flanges are so shaped that they leave the opening, represented on the diagram by the broken "O"-shaped polygonal outline O (FIG. 2), entirely clear of any obstacle.

The mechanism proper consists of a sliding member, moving between two flanges 1 and 1' in such a way as to have one degree of freedom: i.e. translation on its main axis Y. The mechanism also comprises levers 3, 4, 3b, and 4b and connecting rods 6, 6b, 7, 7b.

The levers and connecting rods: respectively, 3 and 3b, 4 and 4b, 5 and 5b, 6 and 6b, are symmetrically related to axis Y. On account of this symmetry and for reasons of clarity, only levers 3 and 4 and connecting rods 5 and 6 will be described. Lever 3 is pivotally mounted at articulation A in between flanges 1 and 1', about which it can pivot freely. Lever 4 is pivotally mounted at articulation B in between the flanges 1 and 1', about which it can pivot freely. In addition, lever 3 articulates at 3A and lever 4 articulates at 4B. Connecting rods 6 and 7 are fitted at the articulation points 3A and 4B. At their other end, the said connecting rods are linked to the sliding member 2 at articulation points 2A and 2B.

As shown in FIG. 2, the downward movement of the sliding member 2 induces, by interaction of related points described above, and by means of the connecting rods, the rotation of levers 3 and 4.

That portion of the levers which is external to the flanges is in the shape of a circular arc, centered on the articulation point. In this way, when the apparatus is being opened, there is no relative lateral movement between the levers and the flanges and any risk of tearing or pinching the surrounding tissue is thereby obviated.

Blades D1 to D5. The said blades are fitted perpendicularly to the ends of levers 3, 3b, 4, 4b, and to the sliding member 2. Their length is adaptable, according to requirements. They can, for example, be 12 cm. long.

While the apparatus is still in a closed position, the said blades are introduced into the cavity or incision. The translation of the sliding member induces the rotation of the levers. The sliding member and the levers actuate the blades, which bring about the widening of the incision or cavity, outline O.

Figures 6, 6B:
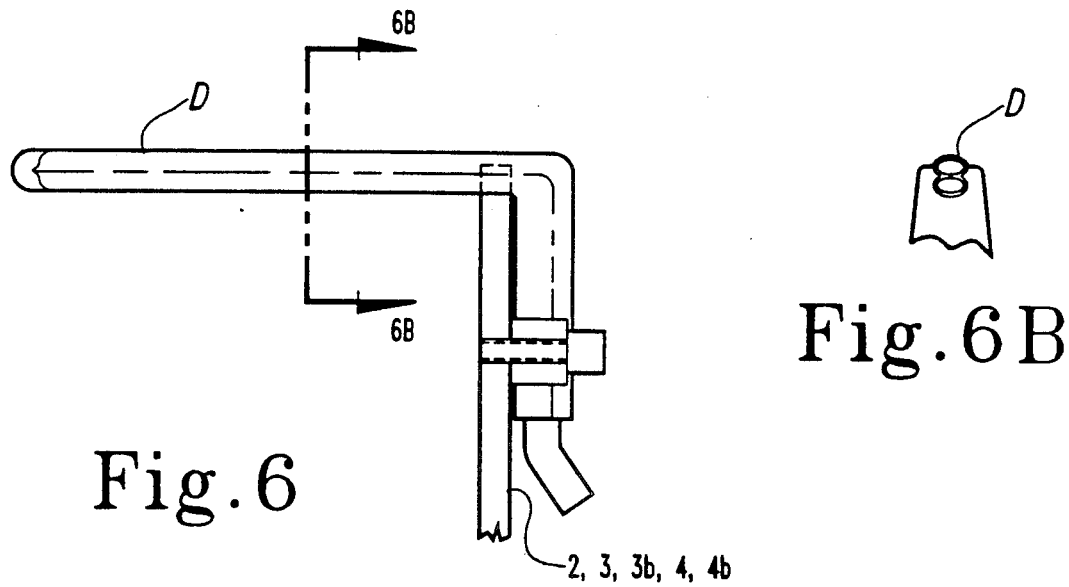
FIG. 6 is a side view of a blade mounted to a lever of the retractor of FIG. 1.
FIG. 6B is a sectional view of the blade of FIG. 6 taken along a line and view in the direction of arrow B.

The blades can have a permanent fixation or they can be dismountable, for adjustment to each different case. They can be hollow, thereby serving to draw out laser fumes; or to carry optical fibers for lighting purposes, thus greatly improving the visual field inside the cavity or incision, without causing any additional obstruction. (See FIG. 6.)

The blades can be polygonal, with grooves or rails, in which or on which it is possible to attach accessories for a surgical operation. (See FIG. 6.)

The opening and closing device. The said device controls the translation of the sliding member 2 and works on a crank system. The crankshaft 8 is pivotally mounted at articulation C, in between flanges 1 and 1', about which it can pivot freely. The crank-handle m of the crankshaft is engaged in a hole in one end of the sliding member 2. As we know, the rotation of the crankshaft drives the sliding member.

Figure 4:
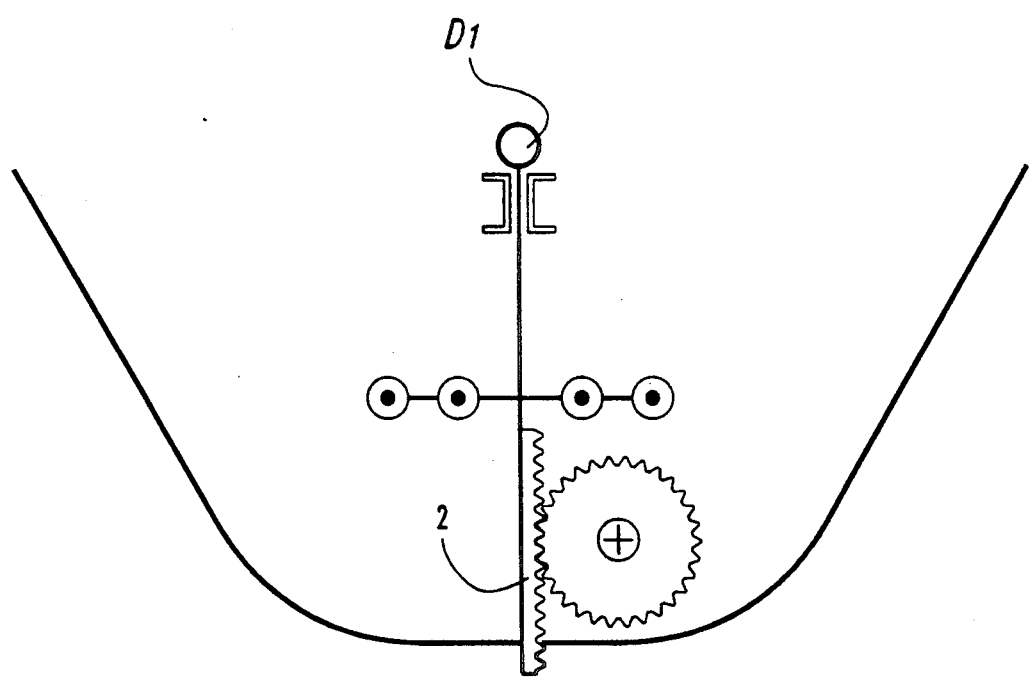
FIG. 4 is a fragmentary, diagrammatic front view of the retractor of FIG. 1 only showing a rack and pinion drive mechanism.
Figure 5:
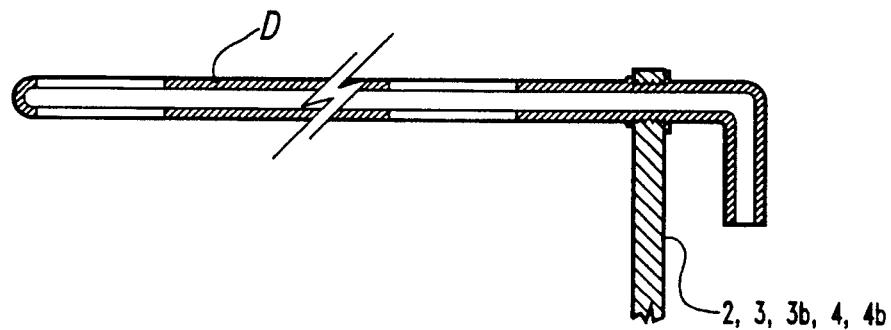
FIG. 5 is a sectional view of a blade mounted to a lever of the retractor of FIG. 1.

The aforesaid operation could equally well be carried out by a rack and pinion system. (See FIG. 4)

A possible variation on this would be to use a screw and nut system, the nut being an integral part of the sliding member, and the screw fixed in a translatory axis in relation to the box formed by the flanges.

The screw can be rotated manually or by a low-voltage, electric screwdriver, for example, operating on a rechargeable battery, easily available on the market. To obtain any possible degree of opening, if one has chosen to use a reversible device, a ratchet or any other known locking device will be added to hold the crankshaft in an intermediate position. (See FIG. 7, where such a system is shown.)

Once the required degree of opening has been obtained, the locking device is left in place until the surgery or examination has been completed. The locking system is then released and the retractor thereafter closed by the opposite maneuver to that used to open it.

Second Type of Design

Figure 8:
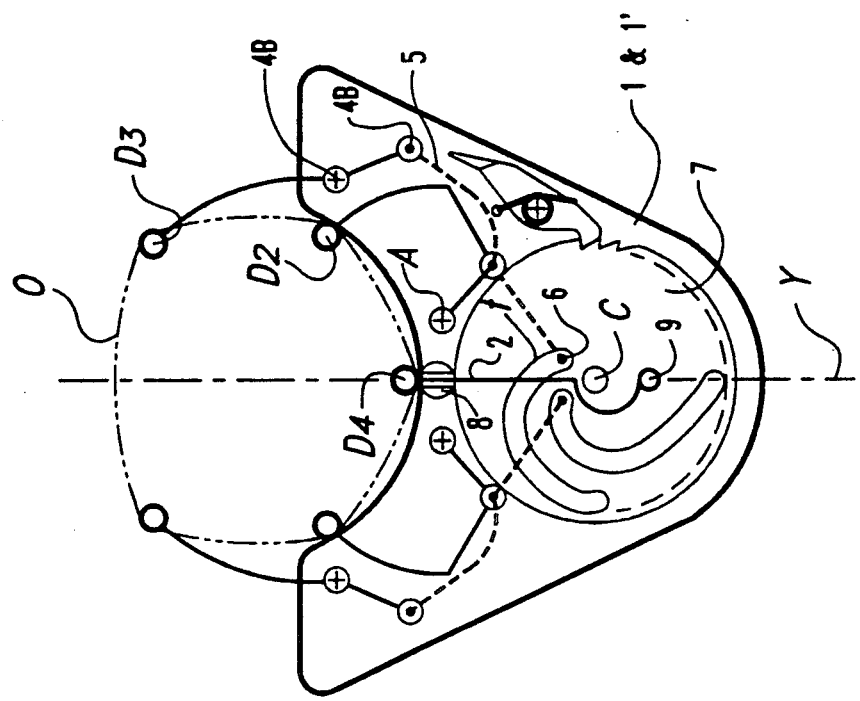
FIG. 8 is diagrammatic front view of an alternate embodiment of the medical retractor of FIG. 7 with an added blade and showing the retractor in the open position.
Figure 7:
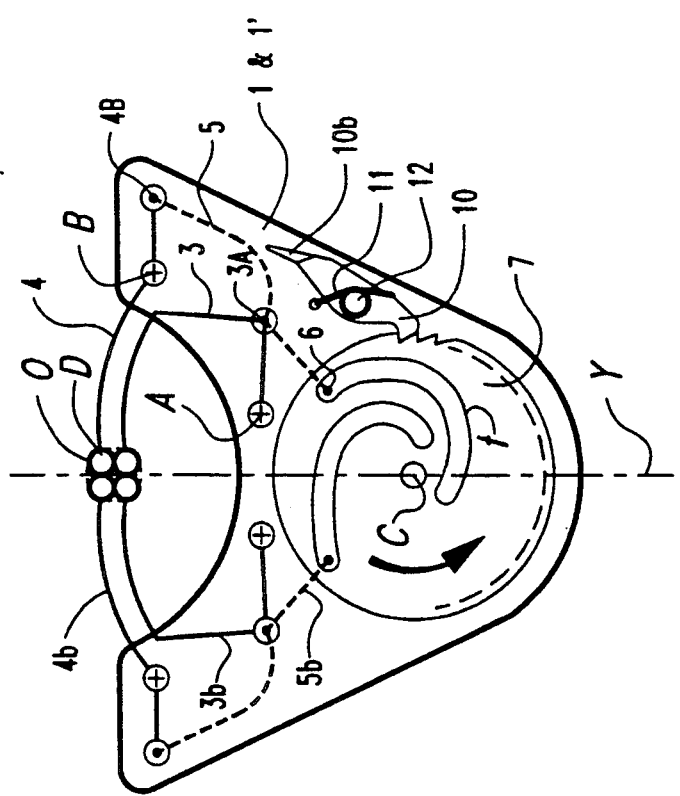
FIG. 7 is a diagrammatic front view of an alternate embodiment of the medical retractor in the closed position.

The second type of retractor design relating to the present invention is shown as follows:

FIG. 7, front view, closed position.
FIG. 8, front view, open position.

In this particular design, the apparatus has four components, including:

A box (to support the mechanism), comprising two flanges 1 and 1'.

These flanges, which are about 12 cm. in height, about 16 cm. in width and to the order of 2 mm. thick, are kept apart by spacers, (not shown on the diagram).

The box thus formed has a total thickness of around 1.6 cm. The flanges are so shaped that they leave the cavity or incision opening, represented on the diagram by the broken "O"-shaped polygonal outline, entirely clear.

The mechanism properly comprises levers 3, 3b, 4, 4b and connecting rods 5 and 5b. The said levers and connecting rods 3 and 3b, 4 and 4b, 5 and 5b, respectively, are symmetrically related to the axis Y. On account of this symmetry and for reasons of clarity, only levers 3 and 4 and connecting rod 5 will be described. Lever 3 is pivotally mounted at articulation A, in between flanges 1 and 1', about which it can pivot freely. Lever 4 is pivotally mounted at articulation B, in between flanges 1 and 1', about which it can pivot freely. In addition, lever 3 has an articulation point at 3A and lever 4 has an articulation point at 4B. Connecting rod 5 is linked to these articulation points. At one end of the said connecting rod, there is a roller inside the groove of a cam 7.

The blades, which are identical to those blades used on the first version, are implanted as previously described.

The opening and closing device.

The groved cam 7 pivots about a shaft C, which is positioned by bearings in between flanges 1 and 1' and directly linked to a nurled handle control system, identical to that shown on FIG. 3.

As shown in FIG. 8, the anti-clockwise rotation of the cam drives the end of the connecting rods 5 and 5b and thereby brings about the lateral movement of the said connecting rods. This movement in turn drives the levers, which, as on the first version described above, carry the blades.

The second version, which we are describing here, has four blades, and can form a quadrilateral opening.

On FIG. 8, we see how to form a pentagonal opening by adding a sliding member 2, guided through a pivotally mounted shaft 8 and connected at its lower end to the opening and closing device by a handle 9. The rotation of the cam 7 directly induces the opening or closing of the said sliding member, which, as on the previously described first version, is fitted with a blade D1.

In addition, FIGS. 7 and 8 show a ratchet system, which locks the return mechanism and holds the retractor open at any intermediate position. The ratchet 10 can pivot freely about a shaft 12, fixed between flanges 1 and 1'. Contact is renewed between the ratchet 10 and the cam 7 by means of a spring 11.

The exterior of the cam has a plurality of dissymetrical notches such that, for each anti-clockwise rotation of the cam, the said notches raise the ratchet-wheel, whilst, for each clockwise rotation, they block against the ratchet-wheel, thereby immobilizing it.

A boss 10b can be integrated at the back of the ratchet, thereby allowing for manual release of the said ratchet and hence for rotation in the opposite direction, essential for the closing of the apparatus.

With two types of retractor design previously described, the apparatus is presented laterally to the cavity or incision opening and is therefore better suited for use in cavity examination: in particular, in gynecology, for examination of the vagina and of the cervix.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A retractor for holding open an opening in the human body comprising:
   a main frame having a forward end with a recess formed therein;
   a plurality of levers pivotally mounted to said main frame and having distal ends;
   a pair of upper fingers mounted to a pair of said distal ends and extending perpendicularly outwardly from said main frame;
   a pair of middle fingers mounted to a second pair of said distal ends and extending perpendicularly outwardly from said main frame;
   a slide movably mounted to said main frame and having an outer end, said slide movable along a straight line;
   a lower finger mounted to said outer end and extending perpendicularly outwardly from said main frame; and,
   a control means movably mounted to said main frame and connected to said levers and slide, said control means having a first position moving said levers and slide to locate said upper fingers, said middle fingers and said lower finger in a closed position ready for insertion into said opening in the human body and further having a second position moving said levers and slide to pivotally move and locate said upper fingers and said middle fingers and to linearly move and locate said lower finger in an open position spreading and holding human tissue apart surrounding said opening.

2. The retractor of claim 1 wherein:
   said levers are movably mounted on said main frame to move said fingers in arcuate paths as said fingers move between said closed position and said open position.

3. The retractor of claim 2 wherein:
   said levers are pivotally mounted to said main frame about fixed pivot axes.

4. The retractor of claim 3 wherein: said fingers are removably mounted to said levers.

5. The retractor of claim 1 wherein:
   said main frame includes a pair of spaced apart plates between which said slide is slidably mounted, said slide includes a longitudinal axis extending in the direction of movement of said slide; and,
   said pair of upper fingers and said pair of middle fingers are symmetrically arranged relative to said longitudinal axis.

6. The retractor of claim 5 wherein:
   said levers are movably mounted between said spaced apart plates and are connected to said slide, said levers include portions which extend external of said plates to said upper fingers and said middle fingers with said portions having the shape of a circular arc.

7. The retractor of claim 6 wherein:
   said control means include a plurality of rods connecting said slide to said levers, said rods move with said slide pivoting said levers with said upper fingers and said middle fingers while said lower fingers moves along said axis.

8. The retractor of claim 7 wherein:
said rods are mounted and are positioned between said plates.

9. The retractor of claim 1 wherein:
said control means is operable to move said upper fingers, said middle fingers and said lower finger relative to said main body.

10. A retractor for holding open an opening in the human body comprising:
a main frame;
a plurality of levers pivotally mounted to said main frame and having distal ends;
a pair of upper fingers mounted to said distal ends and extending perpendicularly outwardly from said main frame;
a slide movably mounted to said main frame and having an outer end, said slide movable along a straight line;
a lower finger mounted to said outer end and extending perpendicularly outwardly from said main frame; and,
a control means movably mounted to said main frame and connected to said levers, and control means having a first position moving said levers and slide to locate said upper fingers and said lower finger in a closed position ready for insertion into said opening in the human body and further having a second position moving said levers and slide to pivotally move and locate said upper fingers and to move said lower finger along a straight line and in an open position spreading and holding human tissue apart surrounding said opening; and wherein: said main frame includes a pair of spaced apart plates between which said slide is slidably mounted, said slide includes a longitudinal axis extending in the direction of movement of said slide; said pair of upper fingers are symmetrically arranged relative to said longitudinal axis; said levers are movably mounted between said spaced apart plates and are connected to said slide, said levers include portions which extend external of said plates to said fingers with said portions having the shape of a circular arc; and, said control means includes a plurality of rods connecting said slide to said levers, said rods move with said slide pivoting said levers with said upper fingers while said lower finger moves along said axis.

11. The retractor of claim 10 wherein:
said rods are mounted and are positioned between said plates.

* * * * *